United States Patent
Hofmann et al.

(10) Patent No.: US 9,726,588 B2
(45) Date of Patent: Aug. 8, 2017

(54) FLOW CONTROL IN A MICROFLUIDIC DEVICE

(75) Inventors: Oliver Hofmann, London (GB); Simon Rattle, Woking (GB); Claire Walshe, Ealing (GB)

(73) Assignee: Molecular Vision Limited, London (GB)

( * ) Notice: Subject to any disclaimer, the term of this patent is extended or adjusted under 35 U.S.C. 154(b) by 661 days.

(21) Appl. No.: 14/238,390

(22) PCT Filed: Aug. 10, 2012

(86) PCT No.: PCT/EP2012/065695
§ 371 (c)(1),
(2), (4) Date: May 27, 2014

(87) PCT Pub. No.: WO2013/024030
PCT Pub. Date: Feb. 21, 2013

(65) Prior Publication Data
US 2014/0260559 A1    Sep. 18, 2014

(30) Foreign Application Priority Data
Aug. 12, 2011  (GB) .................................. 1113990.4

(51) Int. Cl.
*G01N 11/02* (2006.01)
*G01N 13/02* (2006.01)
*B01L 3/00* (2006.01)

(52) U.S. Cl.
CPC ........ *G01N 11/02* (2013.01); *B01L 3/502746* (2013.01); *G01N 13/02* (2013.01); *B01L 2300/0681* (2013.01); *B01L 2300/088* (2013.01); *B01L 2300/0816* (2013.01); *B01L 2400/0406* (2013.01); *B01L 2400/086* (2013.01); *B01L 2400/088* (2013.01)

(58) Field of Classification Search
CPC ......... B01L 3/502746; B01L 2300/088; B01L 2400/0406; B01L 2400/0457; B01L 2400/08; B01L 2400/084; B01L 2400/086; B01L 2400/088; B01L 2400/0688
See application file for complete search history.

(56) References Cited

U.S. PATENT DOCUMENTS

| 5,458,852 A | 10/1995 | Buechler |
| 6,613,560 B1 | 9/2003 | Tso et al. |
| 6,669,831 B2 * | 12/2003 | Chow ................. B01J 19/0093 137/804 |
| 2005/0136552 A1 * | 6/2005 | Buechler ........... B01L 3/502746 436/514 |
| 2006/0207880 A1 | 9/2006 | Joyce et al. |
| 2007/0036684 A1 | 2/2007 | Burkhardt |
| 2007/0099290 A1 | 5/2007 | Iida et al. |
| 2008/0190220 A1 * | 8/2008 | Backes ................ B29C 66/542 73/864.81 |

FOREIGN PATENT DOCUMENTS

| JP | 2009-031102 | 2/2009 | |
| WO | WO 9217769 A1 * | 10/1992 | .......... G01N 33/585 |
| WO | 01/57509 | 8/2001 | |
| WO | 01/86249 | 11/2001 | |
| WO | 2010/122158 | 10/2010 | |
| WO | 2011/087813 | 7/2011 | |

OTHER PUBLICATIONS

Atencia, Javier et al. "Controlled microfluidic interfaces." Nature (2005) 437 648-655.*
Great Britain search report dated Dec. 14, 2011 regarding Application No. GB1113990.4.
International Search Report and Written Opinion dated Dec. 11, 2012 for International Application No. PCT/EP2012/065695 filed Aug. 10, 2012.

* cited by examiner

*Primary Examiner* — Christopher A Hixson
(74) *Attorney, Agent, or Firm* — McDonnell Boehnen Hulbert & Berghoff LLP

(57) ABSTRACT

This invention relates to a method of inducing fluid flow in a passive capillarity filled microfluidic device involving the use of a dual flow control reagent system, wherein the first flow control reagent is a surfactant which reduces surface tension of an aqueous fluid sample and the second flow control reagent is a viscosity enhancer.

19 Claims, 2 Drawing Sheets

FLOW CONTROL IN A MICROFLUIDIC DEVICE

This application is a U.S. national phase application of International Patent Application No. PCT/EP2012/065695 filed on Aug. 10, 2012, which claims the benefit of Great Britain patent application 1113990.4, filed Aug. 12, 2011.

FIELD

This invention relates to a method of inducing fluid flow in a passive capillarity filled microfluidic device involving the use of a dual flow control reagent system, wherein the first flow control reagent is a surfactant which reduces surface tension of an aqueous fluid sample and the second flow control reagent is a viscosity enhancer.

BACKGROUND

The accurate control of fluid flow in microfluidic devices is key to the ability to perform assays, for example diagnostic immunoassays in a microfluidic device. Fluid flow can be achieved with actuated or passive microfluidics. Actuated microfluidics control fluid flow using an external power source or pump. In passive microfluidics, fluid flow is encoded by the design of the microfluidic device itself rather than any externally applied forces, with fluid flow occurring due to capillary forces. Passive microfluidic devices are attractive due to their low power consumption, portability and low dead volume.

The optimization of performance of assays conducted in microfluidic devices is dependent on control of the timings of fluid residence in various portions of a microfluidic channel, where various assay steps are performed. Frequently, this is controlled by the incorporation of structural delay elements, such as delay loops that take a controlled period of time to fill. In addition, fluid composition itself affects flow characteristics. For example, the use of surfactants provides surface wetting properties that allow fluid flow in a microfluidic channel under passive capillarity.

In general, a higher surfactant concentration leads to a faster flow rate and consequently a shorter residence time within a microfluidic channel. However, a problem is observed for very narrow channels, which have a high surface area to volume ratio. As a fluid front moves along such a channel, its surfactant content becomes depleted as the channel/fluid interface is continually coated with surfactant. This depletion of surfactant content results in a gradual slowing of fluid flow along the channel. Increasing the surfactant concentration to compensate for this can give erratic fluid flow rates which are too fast to provide precise control and are vulnerable to non-uniform filling patterns, incomplete wetting of channel walls and air bubble formation if there are even minor variations in dimensions or surface irregularities from chip-to-chip. In addition, the flow rate of fluid within a microfluidic channel is very sensitive to small changes in concentration of surfactant. Differences in flow rate give rise to poor precision of tests carried out in a microfluidic device. In a commercial setting, low-cost (e.g. injection moulded from thermoplastic polymer) microfluidic components are required and a means of improving the consistency of fluid flow is necessary in order to achieve acceptable test precision.

It has now been determined that these problems can be overcome by using a dual flow control reagent mixture that provides uniform wetting of microfluidic channel walls and predictable fluid flow rate.

SUMMARY

According to a first aspect of this invention, there is provided a method of flowing a fluid sample through a microfluidic channel in a passive microfluidic device by capillarity, the method comprising:
  providing a passive microfluidic device comprising an inlet reservoir, an outlet reservoir and a microfluidic channel having an inlet and an outlet and extending between the inlet reservoir and the outlet reservoir, wherein at least one portion of the channel is provided with a structural feature arranged to decrease or increase flow rate of a fluid through the channel;
  introducing an aqueous fluid sample into the inlet reservoir and allowing the fluid sample to flow via the inlet through the channel by capillarity to the outlet,
  wherein the method comprises the step of adding first and second flow control reagents to the fluid sample within the inlet reservoir or prior to introduction of the fluid sample into the inlet reservoir, and
  wherein the first flow control reagent is a surfactant which reduces the surface tension of the fluid sample and the second flow control reagent is a viscosity enhancer.

The method of the invention utilizes a dual flow control reagent system to allow control of flow rate with a surfactant which reduces surface tension of the aqueous fluid sample and control of flow consistency through adjustment of fluid viscosity with a viscosity enhancer. The combined effect of a first flow control reagent which reduces surface tension of the aqueous fluid sample and a second flow control reagent which is a viscosity enhancer provides controlled flow under conditions where a surfactant concentration is present to enhance flow rate at a concentration which would otherwise lead to erratic fluid flow, non-uniform filling, air bubbles and the like. Thus, the method enables control of fluid flow rate and complete wetting of the microfluidic channel walls without air bubbles in complex microfluidics, as is required for control and optimisation of, e.g., diagnostic immunoassays performed thereon.

In an embodiment of the invention, the method comprises mixing at least one of the first and second flow control reagents with the fluid sample prior to introduction of the fluid sample into the inlet reservoir. The method may comprise mixing both the first and second flow control reagents with the fluid sample prior to introduction into the inlet reservoir.

In another embodiment of the invention, the method comprises introducing the fluid sample into the inlet reservoir, wherein at least one of the first and second flow control reagents is pre-deposited within the inlet reservoir. The first and second flow control reagents may both be pre-deposited within the inlet reservoir. In this embodiment addition of flow control reagents to the fluid sample occurs as pre-deposited flow control reagent is solubilised by the fluid sample. At least one of the first and second flow control reagents may be impregnated on a matrix (such as a filter) located within the inlet reservoir prior to introduction of the fluid sample into the inlet reservoir. Accordingly, the method may comprise the steps of impregnating a matrix (such as a filter) with the first and/or second flow control reagent and positioning the matrix in the inlet reservoir, preferably adjacent the inlet. Impregnation may be carried out before or after positioning the matrix in the inlet reservoir. As the fluid sample flow from the inlet reservoir, via the inlet, into the channel, it contacts and/or passes through the matrix solubilising the flow control reagent(s) impregnated thereon.

The matrix comprises a material within which the first and second flow control reagents may be impregnated. In use, addition of the first and second flow control reagents to a sample fluid occurs by contact of the sample fluid with the impregnated matrix in the inlet reservoir and/or passage of the sample fluid through the matrix. In some embodiments, the matrix is a filter (for example, a whole blood filter). In some embodiments, the matrix is located adjacent the inlet. In some embodiments, the matrix comprises a glass fibre filter.

The first flow control reagent may be a surfactant, for example, selected from the group consisting of, but not limited to polyoxyethylene sorbitan esters (e.g. TWEEN™ surfactants such as Tween 20), nonylphenol ethoxylate or secondary alcohol ethoxylates (e.g. TERGITOL™ surfactants) and octylphenol ethoxylates (e.g. TRITON™ surfactants such as Triton X-100).

The first flow control reagent may be added in amount to give to a concentration of 0.01 to 2% (w/v) based on the sample fluid volume.

The second flow control reagent may be a surfactant viscosity enhancer or a non-surfactant viscosity enhancer.

Suitable surfactant viscosity enhancers include polyoxyethylene fatty ethers (e.g. BRIJ™ surfactants such as BRIJ 98 and BRIJ S100).

Suitable non-surfactant viscosity enhancers include hydrophilic polymers, for example, cellulose derivatives (such as methyl cellulose and methylcellulose derivatives, including hydroxypropylmethylcellulose, and hydroxyethyl cellulose), proteins (such as gelatin, albumin and globulin), polyethyleneoxide polymers (POLYOX™), polysaccharides (such as dextran, glycogen, xanthan gum, alginates (e.g. sodium alginate), hyaluronates, pectin, chitosan, agarose and amylose), cyclodextrins, monosaccharides and disaccharides (such as glucose, mannose, galactose, altose, sucrose, lactose, trehalose and maltose), oligosaccharides and polypeptides.

The second flow control reagent may be added in an amount to give a concentration of 0.01 to 5% (w/v) based on the volume of the fluid sample, preferably 0.1 to 5%.

In some embodiments, the first control reagent and the second control reagent are added in a ratio of 1:10 to 10:1 (by weight), preferably 1:7.5 to 5:1, more preferably 1:5 to 5:1, even more preferably 1:5 to 2.5:1.

In embodiments where both the first control reagent and the second control reagent are surfactants, the first fluid control reagent is preferably added to give a concentration of 0.01 to 1% (w/v) and the second flow control reagent is preferably added to give a concentration of 0.1 to 5% (w/v), based on the volume of the fluid sample.

In an embodiment of the invention, the microfluidic channel defines at least one detection zone. A detection zone is a portion of the channel in which the fluid sample resides whilst detection of an analyte within the fluid sample occurs or whilst a reference measurement is taken.

In any of the above embodiments of the invention, each occurrence of a structural feature of the channel arranged to decrease or increase fluid flow rate may be independently selected from the group consisting of, but not limited to, a looped portion of the channel (a delay loop), a narrowing or widening in channel width, an increase or decrease in any cross-sectional dimension of the channel (e.g. channel depth or width), or a variation in material forming a portion of the channel walls. Preferably the channel is provided with at least one delay loop, wherein the portion of the channel forming the delay loop has at least one cross-sectional dimension (depth or width) which is smaller than the portions of the channel adjoining the delay loop. Looping or meandering channel configurations as opposed to longer straight channels are typically employed to minimise the microfluidics foot-print to yield smaller compact devices.

The passive microfluidic device may comprise a substrate (preferably a monolithic substrate) within which the inlet reservoir, inlet, outlet reservoir, outlet and microfluidic channel are formed, and a seal. The microfluidic channel is defined by channel walls. The substrate may be formed of a thermoplastic, for example PMMA, polycarbonate, a polyolefin or polystyrene. The substrate may be injection moulded. In certain embodiments, the substrate is formed from a dye-doped material. This enables the substrate itself to act as an optical filter. The seal may be formed from a tape sealed by an adhesive or laser welding and may comprise, for example, the same material as the substrate. It will be appreciated that a variety of material choices could be made for both the substrate and seal.

In some embodiments, probing for detection of the presence of an analyte is conducted at one or more points along the microfluidic channel. This probing may comprise, for example, optical detection of an analyte.

In a second aspect, the invention provides a kit comprising:

a) a passive microfluidic device comprising an inlet reservoir, an outlet reservoir and a microfluidic channel having an inlet and an outlet and extending between the inlet reservoir and the outlet reservoir, wherein at least one portion of the channel is provided with a structural feature arranged to decrease or increase capillary flow rate of a fluid through the channel; and b) first and second flow control reagents, wherein the first flow control reagent is a surfactant which reduces the surface tension of a fluid and the second flow control reagent is a viscosity enhancer.

In some embodiments, the kit further comprises instructions for use of the kit in a method according to the first aspect of the invention.

Preferred features of the first aspect of the invention also apply to the second aspect mutatis mutandis. Accordingly, structural features of the device and identity and composition of the flow control reagents as described for the first aspect of the invention also apply to the second aspect of the invention.

In a third aspect, the present invention provides a passive microfluidic device comprising an inlet reservoir, an outlet reservoir and at least one microfluidic channel having an inlet and an outlet and extending between the inlet reservoir and the outlet reservoir, wherein the microfluidic device further comprises a filter impregnated with a first flow control reagent and a second flow control reagent and located within the inlet reservoir, wherein the first flow control reagent is a surfactant capable of reducing the surface tension of an aqueous fluid and the second flow control reagent is a viscosity enhancer.

The matrix comprises a material within which the first and second flow control reagents may be impregnated. In use, addition of the first and second flow control reagents to a sample fluid occurs by contact of the sample fluid with the impregnated matrix in the inlet reservoir and/or passage of the sample fluid through the matrix. In some embodiments, the matrix is a filter (for example, a whole blood filter). In some embodiments, the matrix is located adjacent the inlet. In some embodiments, the matrix comprises a glass fibre filter.

Preferred features of the first aspect of the invention also apply to the third aspect mutatis mutandis. Accordingly, structural features of the device and identity and composition of the flow control reagents as described for the first aspect of the invention also apply to the third aspect of the invention.

BRIEF DESCRIPTION OF THE DRAWINGS

Specific embodiments of the invention are described below by way of example only and with reference to the accompanying drawings, in which.

DETAILED DESCRIPTION

Figure 1:
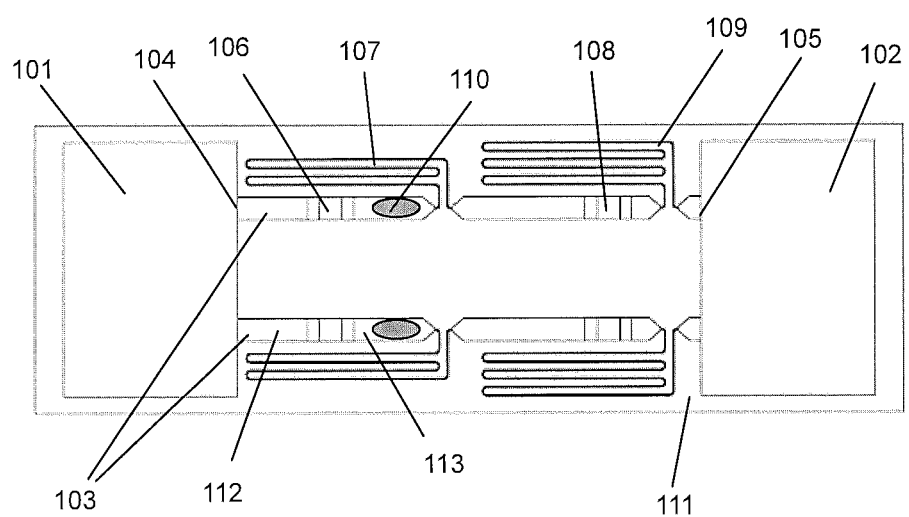
FIG. 1 shows a schematic view of a two channel microfluidic device.

A microfluidic device according to the present invention is a device comprising at least one microfluidic channel having at least one dimension of less than 5 mm, preferably less than 1 mm. The at least one dimension may be a cross-section dimension (i.e. the channel depth or width) at any position along the length of the channel. It will be appreciated that other dimensions of the channel and device may exceed this value. The cross-section is taken perpendicular to the direction of fluid flow within a channel.

A passive microfluidic device is a microfluidic device in which fluid flow in the device is encoded by forces inherent to the structure and composition of the device and the composition of the fluid (i.e. capillary and wicking forces). In such devices external forces (such as pumping, application of an electronic field, application of a pressure differential) are not required to create fluid flow through the device. In the methods of this invention, flow of a fluid sample through the channel occurs by virtue of capillarity and wicking and preferably no additional external forces are applied. Capillary flow in the channel is enabled by the inclusion of a surfactant (the first flow control reagent) and is further controlled by the additional inclusion of a second flow control reagent.

A fluid sample in the context used herein is an aqueous fluid, i.e. a fluid comprising water and optionally additional components such as an analyte for detection. A fluid in this context is taken to mean a liquid.

The present disclosure relates to a method for flowing a fluid sample through a microfluidic channel of complex structure, i.e. wherein at least one portion of the channel is provided with a structural feature arranged to decrease or increase capillary flow rate of a fluid through the channel. The structural feature may be any physical feature of a portion of the channel (e.g. configuration, dimensions or material) which causes a decrease or increase of the flow rate of the fluid through the channel, compared to the flow rate of a corresponding channel in the absence of the structural feature. The structural feature may be selected from the group consisting of, but not limited to, a looped portion of the channel (a delay loop), a narrowing or widening in channel width, an increase or decrease in any cross-sectional dimension of the channel (e.g. channel depth or width), or a variation in material forming a portion of the channel walls. A looped portion of the channel (delay loop) is a non-linear portion of the channel through which fluid flowing through the channel must pass. The looped portion departs from and then rejoins the path formed between the inlet and the outlet by portions of the channel not comprising delay loop(s). The path formed by portions of the channel not comprising delay loop(s) may, for example, be a linear path between the inlet and outlet.

It will be appreciated that the invention also contemplates a method of flowing a fluid sample through a microfluidic channel in a microfluidic device corresponding to any embodiments of the first aspect of the invention in a microfluidic device without a structural feature arranged to decrease or increase fluid flow.

As is well known in the art, BRIJ® surfactants are polyoxyethylene fatty ethers. These can be generally represented by the formula R—[OCH$_2$CH$_2$]$_n$—OH, where R is alkyl and n is 2 or more. In some embodiments, R may be C$_{12-18}$ alkyl and n may be 2 to 100. For example, BRIJ 98 corresponds to polyoxyethylene(20)oleyl ether, where R is C$_{18}$H$_{35}$ and n is 20.

As is well known in the art, TRITON® surfactants are octylphenol ethoxylates and TERGITOL® surfactants are nonylphenol ethoxylates and secondary alcohol ethoxylates. Phenol ethoxylates can be generally represented by the formula:

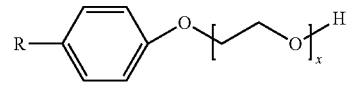

wherein R is octyl (octylphenol ethoxylates) or nonyl (nonylphenol ethoxylates). x represents the ethoxylate repeat unit and is 2 or more, for example 4-70. For example, in Triton X-100, x is 9-10.

It will be understood that a cellulose derivative is a compound derived from cellulose, in which one or more (or preferably all) of the hydroxyl groups of the linked glucose units of cellulose has been replaced by a substituent. In some embodiments, hydroxyl is replaced by —OR, wherein R is, for example, an optionally substituted alkyl group, preferably an alkyl group (e.g. C$_{1-6}$ alkyl) optionally substituted with one or more hydroxyl or carboxyl groups. Exemplary cellulose derivatives include methylcellulose, hydroxypropylmethylcellulose and hydroxyethylcellulose.

As used herein, an oligosaccharide contains 3 to 20 sugar residues. Larger oligosaccharides, containing 11 or more residues are preferred for use as a delay reagent. A polysaccharide contains 21 or more sugar residues. A polypeptide (including proteins) preferably contains more than 20 amino acid residues. It will be appreciated that a polypeptide (or protein) may be glycosylated and/or phosphorylated. Generally, a polymer is taken to be a compound comprising 21 or more monomeric units.

In overview, a sample fluid for testing, containing an unknown quantity of an analyte, is placed in a sample inlet reservoir. The first and second flow control reagents are added to the sample fluid either prior to introduction of sample fluid into the inlet reservoir or within the inlet reservoir, e.g. by exposure to a filter impregnated with flow control reagents positioned therein. Sample fluid is drawn via an inlet into a microfluidic channel by capillarity. Placing of sample fluid within the inlet reservoir may induce a pressure differential within the device. Any pressure differential (or hydrostatic pressure) created by introduction of sample fluid into the device is not considered an externally applied force in the context of this disclosure. Thus, a passive device of the invention preferably does not comprise any means for application of an additional external pressure differential. This is not required in the device because the first and second flow control reagents control flow throughout the device such that no externally applied force is required. The sample fluid flows through the microfluidic channel by capillarity to the outlet and flows through the outlet into an outlet reservoir, by wicking. Probing to allow analyte detection may be conducted at one or more points along the microfluidic channel. These points are referred to herein as detection zones.

A detection zone is a chamber defined by a discrete portion of the microfluidic channel. The detection zone is in fluid communication with the channel and preferably the portion of the channel defining a detection zone has a cross-sectional dimension greater than the corresponding cross-sectional dimension of the adjoining portions of the channel. Probing, for example optical probing, may be carried out on sample fluid within the detection zone. In one embodiment, a light source is utilized to emit light into the detection zone and a light detector is utilized to detect light emission, such as fluorescence or phosphorescence by an optically active material. The optically active material may be an optically active reagent which binds directly or indirectly to the analyte or competes with the analyte for binding to another reagent. A reference detection zone may also be present, in which a reference measurement such as a background light measurement may be taken.

The skilled person will understand that all references to optical and light are made by way of example only and the present disclosure extends to cover other parts of the electromagnetic spectrum. For example, the device in accordance with the present invention is equally suitable for infrared probing using an infrared source and/or infrared detector. In addition, detection techniques other than optical detection can be employed.

Thus, a microfluidic device according to the invention can be used to perform assays to allow detection of an analyte within a fluid sample. Detection techniques are applicable to methods of specific-binding assays for quantitatively or qualitatively assaying analytes. For the avoidance of doubt, "analyte" refers to the species under assay and "specific binding partner" refers to a species to which the analyte will bind specifically.

Examples of analytes and specific binding partners which may be used are given below. In each case, either of the pair may be regarded as the analyte with the other as the specific binding partner: antigen and antibody; hormone and hormone receptor; polynucleotide strand and complementary polynucleotide strand; avidin and biotin; protein A and immunoglobulin; enzyme and enzyme cofactor (substrate); lectin and specific carbohydrate.

Embodiments may relate to a form of immunoassay known as a 2-site immunometric assay. In such assays, the analyte is "sandwiched" between two antibodies, one of which is labelled, directly or indirectly, with an entity that can be measured, e.g by optical or electrochemical means (detection antibody), and the other is immobilised, directly or indirectly, on a solid support (capture antibody).

The skilled person will understand that the present invention is equally applicable to analyses other than in vitro diagnostics, for example environmental, veterinary and food analysis.

It can also be understood that the invention is equally applicable to heterogeneous or homogeneous immunoassays, fluorescent dye binding assays and other assay formats.

The present disclosure relates to a method for flowing a fluid sample through a microfluidic channel of complex structure, enabling control and optimisation of assays performed therein in order to detect the presence of an analyte within the fluid sample. The fluid sample is an aqueous fluid sample which may contain an analyte for detection. The flow control reagents are therefore capable of being solubilised in water (or aqueous solutions) either under ambient conditions or on heating. The fluid sample may range, for example, from aqueous buffer systems (e.g. Bis-Tris buffer) to urine, serum or plasma or filtered whole blood.

Surfactants useful as flow control reagents in the invention should preferably have a hydrophilic-lipophilic balance (HLB) value of 10 or greater. Surfactants with an HLB value of 10 or greater are generally recognised as being water soluble. For example, the HLB value of Triton X-100 is 13.5 and the HLB value for BRIJ 98 is 15.3. A surfactant of this type, when dissolved in an aqueous fluid (water or an aqueous solution) will generally have effects both of decreasing surface tension of the fluid and increasing fluid viscosity. Depending on the identity and concentration of the surfactant, in particular properties such as HLB, molecular weight and chain length, the extent of the effect different surfactants have on surface tension and viscosity varies. Where both the first flow control reagent and the second flow control reagent are surfactants, the surfactants may be selected such that for a given concentration of each surfactant in a defined volume of particular aqueous fluid (for example water) the second flow control reagent will have a greater effect on increasing fluid viscosity than the first flow control reagent. Preferably, the first flow control reagent is selected to also have a greater effect on reducing fluid surface tension than the second flow control reagent. Thus, testing may be carried out to determine a suitable identity for the first and second flow control reagents by: i) providing two or more candidate surfactant solutions, each solution comprising a different surfactant at the same concentration (% w/v) in the same aqueous fluid (e.g. water); ii) testing and comparing the effect on viscosity and optionally surface tension of each surfactant; and iii) assigning surfactants as suitable first and second flow control reagents, respectively, such that in the tested solutions the second flow control reagent has a greater effect on increasing fluid viscosity than the first flow control reagent and, optionally, also that the first flow control reagent has a greater effect on reducing surface tension than the second flow control reagent. The effect of surfactants on viscosity is concentration dependent and may only be evident at concentrations above what might be used just for decreasing surface tension. Thus, the above testing should be carried out at a concentration where an effect on increasing viscosity is observed for at least one of the tested surfactants.

Accordingly, the invention provides a method for identifying first and second flow control reagents for addition to a fluid sample to be flowed through a microfluidic channel, wherein the first and second flow control reagents are each a surfactant, and wherein the method comprises the testing steps set out above. The first and second flow control reagents are preferably identified for use in a method of the first aspect of the invention, a kit of the second aspect of the invention or a device of the third aspect of the invention.

The method of the invention is particularly useful to enable control of fluid flow and filling geometrically complex microfluidic channels. Accordingly, the method may be performed in a device having one or more microfluidic channels and in which each microfluidic channel comprises two or more delay loops having a cross-sectional dimension smaller than the portions of the channel adjoining the delay loops. Each channel may also comprise further variations in a cross-sectional dimension along its length. For example, if the delay loops comprise a narrowing of the channel width, the channel may also comprise variation in its depth at one or more portions. These portions are preferably portions distinct from the delay loops and may be one or more portions of the channel with a depth greater than that of the delay loops. These deeper portions may function as detection zones.

An example of a two-channel microfluidic device in which a method of the invention has been used to successfully control flow of a fluid sample to enable performance of an immunoassay, is shown in FIG. 1. The device comprises an inlet reservoir 101, an outlet reservoir 102 and two microfluidic channels 103 extending therebetween. Each microfluidic channel has an inlet 104 and an outlet 105. It will be appreciated that the device could comprise just a single channel or additional channels, for example a three-channel device. The functioning of this device to perform an assay is based on structural control of residence times of a fluid sample in certain sections of the microfluidic channels. Each of the microfluidic channels 103 defines a first detection zone 106, a first delay loop 107, a second detection zone 108 and a second delay loop 109. In the particular illustrated example a deposit of detection antibody 110 is positioned between the first detection zone 106 and the first delay loop 107 in each channel. The inlet reservoir 101, outlet reservoir 102 and microfluidic channels 103 are defined by an injection moulded substrate 111. In use, a sample is provided into the inlet reservoir 101 and flow of the fluid via the inlets 104, through the microfluidic channels 103 occurs due to capillarity. A dual flow control reagent system is used to control the overall filling time of the device. Flow control reagents are introduced either by mixing with the fluid sample prior to introduction of fluid sample into the inlet reservoir 101 or by adding the fluid sample to a filter pad pre-impregnated with flow control reagents which is placed into the inlet reservoir 101, adjacent to and covering the inlet 104. In that case, sample in the inlet reservoir 101 rehydrates the flow control reagents while passing through the filter on the way to the channel.

Figure 2:
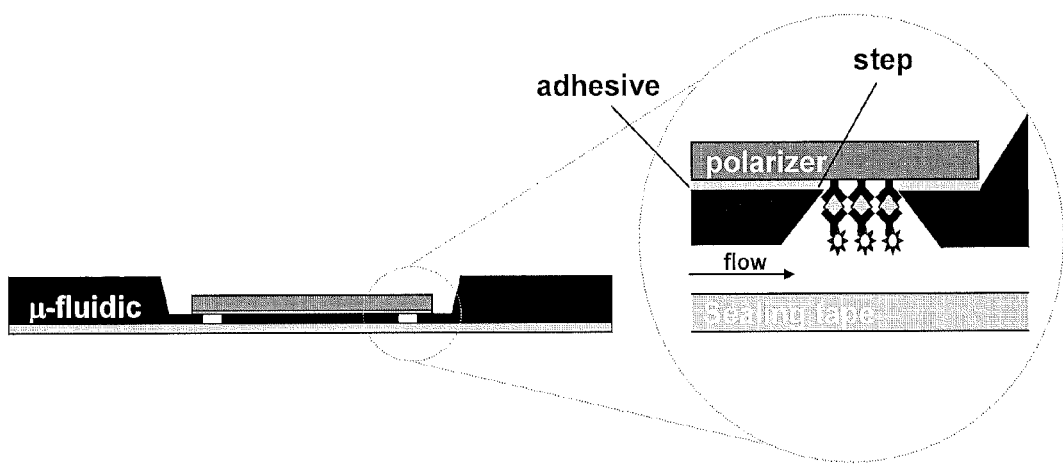
FIG. 2 shows a detailed view of the detection zone of a microfluidic device.

Channel filling is passive and capillarity based, and the addition of a surfactant to a fluid sample is required to lower the surface tension of the fluid sample sufficiently to enable wetting of the microfluidic channel surfaces. For a 2-channel device, as illustrated, the moving flow front of a fluid sample flowing through the microfluidic channels 103 will initially encounter first shallow portion 112, a 2 mm wide and 200 µm deep lane, before ramping into the first detection zone 106, a 500 µm deep chamber. There it may encounter a new material, such as an exposed optical element or adhesive or sealing film for such an element. In the illustrated device an exposed dual brightness enhancement film (DBEF) fixed to the substrate via an adhesive layer is encountered in the detection zone as illustrated in FIG. 2.

After entering the first detection zone 106, where capillarity is reduced due to the increase in channel depth, the fluid front completes filling of the chamber before transitioning back into a second shallow portion 113, a 2 mm wide and 200 µm deep lane. Pre-deposited detection antibody 110 is located within the second shallow portion 113. As the fluid sample reaches the detection antibody, the antibody is rehydrated and transported downstream. The first delay loop 107 (130 µm wide, 200 µm deep) is then designed to provide a sufficient residence time of the fluid sample to enable pre-incubation of detection antibody with analyte in the sample. At the end of the first delay loop 107 the channels widen again towards the second detection zone 108. In the second detection zone 108, the pre-bound analyte-detection antibody complex encounters immobilised capture antibody aimed at capturing the complex. The flow front then moves through the second delay loop 109 which defines the residence time of sample in the second detection zone 108. At the end of the second delay loop 109, the flow front will make contact with a wick placed in the outlet, thereby initiating rinsing to remove unbound detection antibody.

Typically required residence times for assay operation are 4 and 8 min in the first delay loops 107 (pre-incubation) and second delay loops 109 (incubation), respectively, yielding overall chip filling times of <15 min. Also, it needs to be ensured that the detection zones 106, 108 are fully wetted and no air bubbles are enclosed. Furthermore the flow control reagent system should be sufficiently robust to cater for varying surface quality originating from injection moulded chip batches and variations on materials defining channel walls in different portions of the channel, and also to function with a number of sample fluids ranging from aqueous buffer systems to urine, serum, plasma or filtered whole blood.

Typically observed problems with the illustrated 2-channel device when used without the dual flow control reagent method of the invention include the following. First, filling of the deeper detection zones 106, 108 can be problematic. In some cases, fluid preferentially wets the side walls, before merging at the end of the zones towards the exit ramp. This problem is most severe for buffer systems with high surfactant load and consequently low surface tension. Inappropriate conditions can result in incomplete wetting within the detection zones and enclosing of an air bubble, which can be detrimental to detection precision. In the case of incomplete wetting of an active DBEF area this can reduce specific signal. In less severe cases a fluid front asymmetry is observed where fluid progresses faster on one side wall, often resulting in a smaller air bubble forming in the exit ramp area and affecting downstream flow and wicking through-put. The above problems relate to the filling of complex geometric structures.

A second problem can arise in the delay loops, which have a high surface-to-volume ratio. There, partial depletion of surfactant at the flow front can be observed under certain conditions. This is particularly the case in the second delay loop 109, where significant slow-down of filling, even stoppage of flow can occur.

From the above it can be appreciated that there is a trade-off between high surfactant loads to compensate for surfactant depletion in the delay loops and the need for ensuring proper filling of the detection chambers, which is hampered by high surfactant loads. This is balanced by using a dual flow control reagent system comprising one surfactant that reduces surface tension, and a second flow control reagent (preferably also surfactant) which adds a dampening viscosity component to enhance inertia resulting in the fluid passing through the detection chambers without air inclusion.

Thus, contrary to the expectation that surfactant loading sufficient to allow flow through delay loops will lead to erratic filling, if an appropriate choice of a combination of surfactants is utilised, consistent flow is achieved and erratic filling is avoided.

As an example, dual surfactant systems comprising Triton X-100 as the first flow control reagent and BRIJ 98 as the second flow control reagent have been developed and demonstrated to provide suitable flow and filling characteristics in complex microfluidics. Dual surfactant systems have been tested in 2-channel devices of the configuration illustrated in FIG. 1 and also 3-channel devices of a corresponding channel configuration (with a reduced channel width of 1mm, as compared to 2 mm in the 2-channel device). These were observed to overcome the problems seen filling the devices in the absence of dual flow control reagents, whilst fulfilling the specifications in terms of residence times, as required for running immunoassays. For the 2-channel devices 0.2% (w/v) Triton X-100 and 1% (w/v) BRIJ 98 are used. For the 3-channel devices the system was modified to 0.7% (w/v) Triton X-100 and 1% (w/v) BRIJ 98. The surfactants were mixed with fluid sample prior to introduction into the inlet reservoir. In this case, Triton X-100 is used as the surface tension lowering surfactant that is adjusted to yield the required filling times. For the 3-channel device the Triton X-100 load was higher to account for increased surfactant depletion in smaller channels with higher surface-to-volume ratio. For both chips BRIJ 98 acts as a viscosity enhancing flow dampener which enables air bubble free filling of the geometrically complex detection chambers.

In another example the effect of the dual surfactant system Triton X-100 as the first flow control reagent and BRIJ 98 as the second flow control reagent on filling times of aqueous Bis-Tris based buffer solutions been demonstrated on the 3-channel devices. For a fixed 0.5% (w/v) Triton X-100 concentration and BRIJ 98 concentrations of 0.1, 0.2, 0.3 and 0.7% (w/v), 3-channel device filling times of 15, 18, 24 and 40 min were observed, respectively. Here the filling time increase reflects the viscosity enhancing effect of the BRIJ 98. For all conditions filling time CVs were <5% and complete filling of all channel parts was observed.

In another example on the 3-channel devices, a fixed 0.2% (w/v) BRIJ 98 concentration and Triton X-100 concentrations of 0.4, 0.5 and 0.6% (w/v) yielded filling times of 28, 18 and 16 min, respectively. Here the filling time decrease reflects the surface tension reducing effect of Triton X-100. For all conditions filling time CVs were <5% and complete filling of all channel parts was observed.

In another example on the 3-channel chip, the utility of the dual surfactant system was extended from aqueous Bis-Tris based buffer solutions to physiological solutions as commonly used in diagnostic applications. A dual surfactant system of 0.5% (w/v) Triton X-100 and 0.2% (w/v) BRIJ 98 yielded filling times with serum of 20 min as compared to 18 min for aqueous Bis-Tris based buffer solution. The slight increase in filling time is attributed to the increased viscosity of serum compared to aqueous Bis-Tris buffer solution. CVs for the serum filling times were <5% with complete filling of all channel parts.

In another example, Triton X-100 and BRIJ 98 in solution were dried onto a filter pad, as opposed to being spiked into the fluid sample. The surfactant solution is pipetted onto a suitable filter matrix (e.g. whole blood filter membrane VF1 or VF2 from Whatman or conjugate release pad G041 from Millipore), followed by drying in the vacuum oven at 37 deg C. for at least 2 hours. Care has to be taken to compensate for incomplete pick-up of the surfactant by the loaded sample. To this end it was found that for the 2-channel devices with 15×22 mm filters placed into the sample inlet, it was optimal to use concentrations of 0.8% (w/v) Triton X-100 and 4% (w/v) BRIJ 98 in an applied surfactant solution of volume 300 µL for impregnation of the filter.

Throughout this disclosure, where reference is made to an amount of flow control reagent being added to give a specific concentration in % (w/v) in the fluid sample, the amount added is an amount that would give the defined concentration if all flow control reagent were to be solubilised within the fluid sample. In practice, the quantity or concentration use may be tailored according to rate of solubilisation on application of fluid sample.

Embodiments of the invention have been described by way of example only. It will be appreciated that variations of the described embodiments may be made which are still within the scope of the invention.

The invention claimed is:

1. A method of flowing a fluid sample through a micro fluidic channel in a passive micro fluidic device by capillarity, the method comprising:
providing a passive microfluidic device comprising an inlet reservoir, an outlet reservoir and a microfluidic channel having an inlet and an outlet and extending between the inlet reservoir and the outlet reservoir, wherein at least one portion of the channel is provided with a structural feature arranged to decrease or increase capillary flow rate of a fluid through the channel; and
introducing an aqueous fluid sample into the inlet reservoir and allowing the fluid sample to flow via the inlet through the channel by capillarity to the outlet, wherein the method comprises the step of adding first and second flow control reagents to the fluid within the inlet reservoir or prior to introduction of the fluid sample into the inlet reservoir, and
wherein the first flow control reagent is a surfactant which reduces the surface tension of the fluid and the second flow control reagent is a surfactant viscosity enhancer, wherein for a given concentration of each of the first and second flow control reagents in an aqueous fluid the second flow control reagent has a greater effect on increasing fluid viscosity than the first flow control reagent, and
wherein the structural feature of the channel arranged to decrease or increase fluid flow rate is independently selected from the group consisting of a delay loop, an increase or decrease in any cross-sectional dimension of the channel, or a variation in material forming the channel walls.

2. The method of claim 1, wherein the method comprises mixing at least one of the first and second flow control reagents with the fluid sample prior to introduction of the fluid sample into the inlet reservoir.

3. The method of claim 1, wherein the method comprises introducing the fluid sample into the inlet reservoir, wherein at least one of the first and second flow control reagents is pre-deposited within the inlet reservoir, and allowing the at least one of the first and second flow control reagents and the fluid sample to mix following introduction of the fluid sample into the inlet reservoir.

4. The method of claim 3, wherein at least one of the first and second flow control reagents is impregnated on a matrix which is placed within the inlet reservoir prior to introduction of the fluid comprising an analyte into the inlet reservoir.

5. The method of claim 1 wherein the first flow control reagent is a surfactant selected from the group consisting of polyoxyethylene sorbitan esters, nonylphenol ethoxylate or secondary alcohol ethoxylates and octylphenol ethoxylates.

6. The method of claim 1, wherein the first flow control reagent is added to the fluid sample to give a concentration of 0.01 to 2% (w/v), based on the sample fluid volume.

7. The method of claim 1, wherein the surfactant viscosity enhancer is a polyoxyethylene fatty ether.

8. The method of claim 1, wherein the second flow control reagent is added to the fluid sample to give a concentration of 0.01 to 5% (w/v) based on the volume of the fluid sample.

9. The method of claim 1, where any surfactant used as a flow control reagent is a surfactant having an HLB value of 10 or more.

10. The method of claim 9, wherein the method further comprises the step of selecting the surfactants used as the first and second flow control reagents such that for a given concentration (% w/v) of each surfactant in a defined volume of a particular aqueous fluid the first flow control reagent is a surfactant which has a greater effect on reducing surface tension of the fluid than the second flow control reagent.

11. The method of claim 1, wherein the first fluid control reagent is added to give a concentration of 0.01 to 1% (w/v) and the second flow control reagent is added to give a concentration of 0.1 to 5% (w/v), based on the volume of the fluid sample.

12. The method of claim 1, wherein the first flow control reagent is Triton X-100.

13. The method of claim 1, wherein the second flow control reagent is BRIJ 98.

14. The method of claim 1, wherein the first control reagent and the second control reagent are added in a ratio of 1:10 to 10:1 (by weight).

15. The method of claim 1, wherein probing for detection of the presence of an analyte is conducted at one or more points along the microfluidic channel.

16. The method according to claim 1, wherein the microfluidic device further comprises a matrix impregnated with the first flow control reagent and the second flow control reagent and located within the inlet reservoir.

17. The method of claim 16, wherein the matrix is located adjacent the inlet.

18. The method of claim 16, wherein the matrix comprises a filter.

19. The method of claim 1 wherein
the first flow control reagent is a surfactant selected from the group consisting of polyoxyethylene sorbitan esters, nonylphenol ethoxylate or secondary alcohol ethoxylates and octylphenol ethoxylates; and
the surfactant viscosity enhancer is a polyoxyethylene fatty ether.

\* \* \* \* \*